(12) United States Patent  (10) Patent No.: US 7,875,046 B2
Dan  (45) Date of Patent: Jan. 25, 2011

(54) SURGICAL TOOL FOR REMOVING A BLOCK OF TISSUE FROM AN ORGAN

(76) Inventor: Jacob Dan, 22 Devorah Street, Hod Hasharon (IL) 45100

( * ) Notice: Subject to any disclaimer, the term of this patent is extended or adjusted under 35 U.S.C. 154(b) by 932 days.

(21) Appl. No.: 11/744,895

(22) Filed: May 7, 2007

(65) Prior Publication Data

US 2008/0281342 A1    Nov. 13, 2008

(51) Int. Cl.
*A61F 9/00* (2006.01)
*A61B 10/00* (2006.01)

(52) U.S. Cl. ....................... 606/166; 600/564

(58) Field of Classification Search .............. 606/107, 606/166, 167, 131, 132, 161; 600/562, 564, 600/570, 571; 30/279.2, 280
See application file for complete search history.

(56) References Cited

U.S. PATENT DOCUMENTS

| 5,507,772 A | 4/1996 | Shutt et al. |
| 7,041,114 B2 | 5/2006 | Dan |
| 2003/0208217 A1 | 11/2003 | Dan |

*Primary Examiner*—Julian W Woo
(74) *Attorney, Agent, or Firm*—Vladimir Sherman; Professional Patent Solutions

(57) ABSTRACT

A surgical tool for removing a block of tissue or other material from an organ or other body has an elongated support element which carries a first blade assembly including a pair of arms pivotally mounted about a first transverse axis, and a first blade element pivotally mounted to the arms. A second blade element is also pivotally mounted to the support element. A mechanical actuation arrangement is configured to resiliently bias the first blade assembly and the second blade element from in-plane positions towards deflected positions for initiating a predefined cutting sequence for removal of the block of tissue.

20 Claims, 8 Drawing Sheets

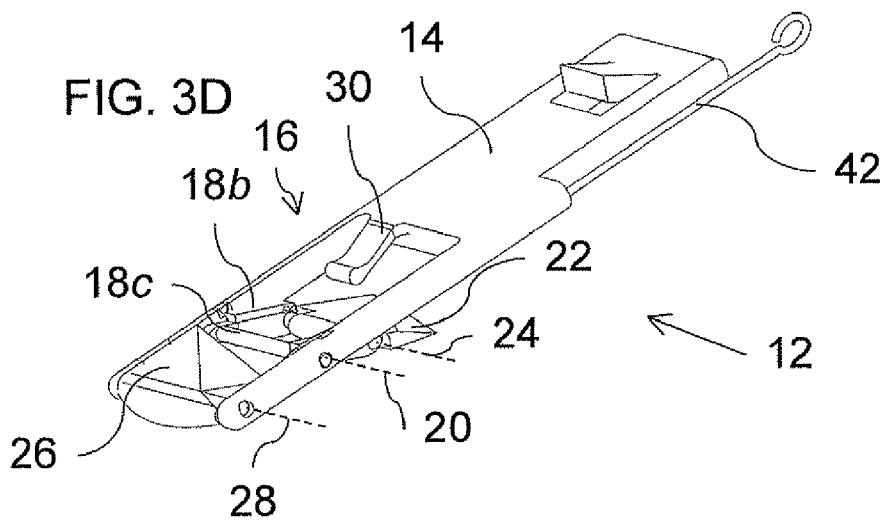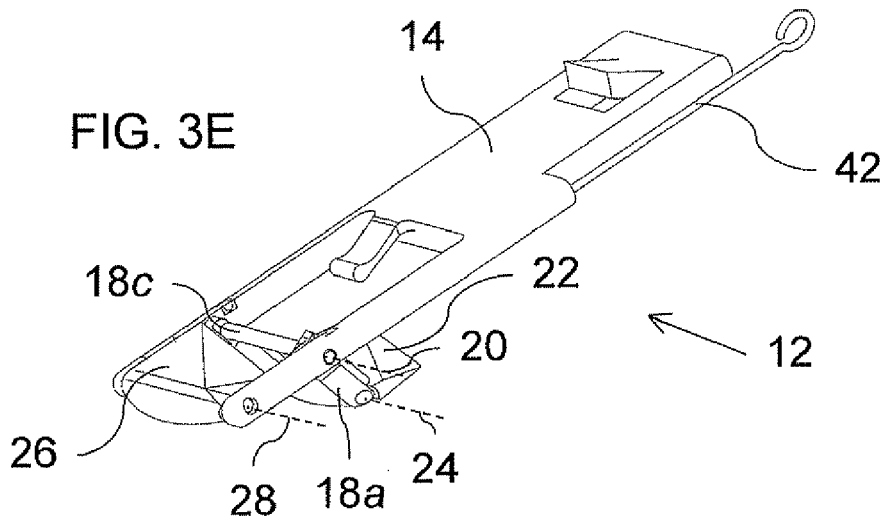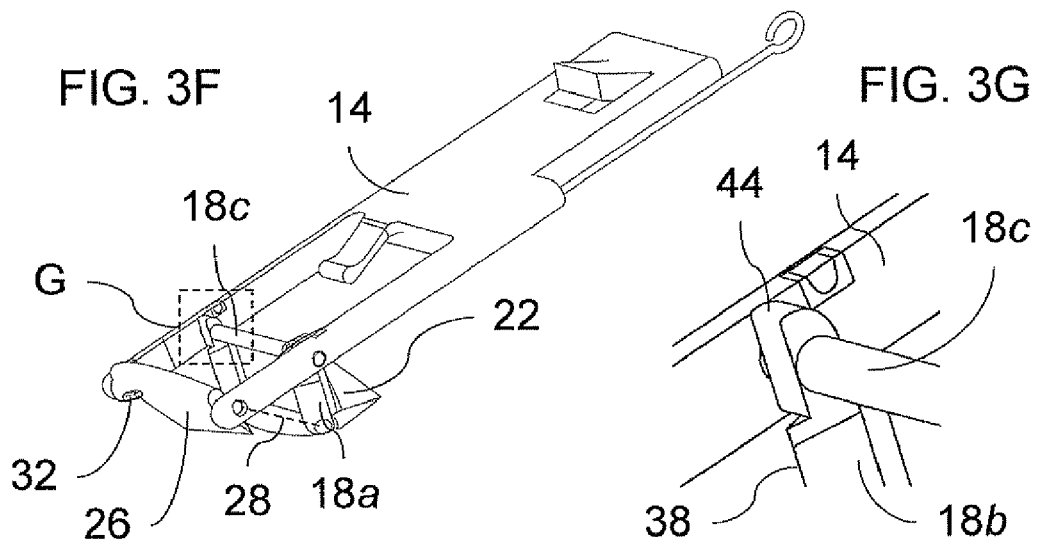

SURGICAL TOOL FOR REMOVING A BLOCK OF TISSUE FROM AN ORGAN

FIELD AND BACKGROUND OF THE INVENTION

The present invention relates to surgical devices and, in particular, it concerns a surgical tool for surgical tool for removing a block of tissue or other material from an organ or other body.

U.S. Pat. No. 7,041,114 to the present inventor describes a surgical method for removing a piece of tissue from within soft body tissue, and particularly, for extracting a tissue block from the angle of the eye, as well as corresponding surgical tools. The technique described therein is highly advantageous, providing reliable extraction of a block of tissue with a well defined shape and dimensions through a small incision. In the context of the ocular surgery procedure described, extraction of a block of trabecular tissue is achieved via a corneal approach through a self-sealing flap, thereby avoiding trauma to vascularized tissue of the eye. The aforementioned patent is hereby incorporated by reference as if fully set out herein.

Despite these advantages, the specific device described in the aforementioned patent relies upon mechanical interaction between shaped blades and the tissue itself in order to direct the path of the blades. More specifically, each blade is formed with a "deflection feature" which is a sharp projection bent towards the surface of the tissue so as to lodge in the tissue and start cutting a slit diverging from the initial insertion slit when moved. While this approach has been found effective, it may be at risk of non-uniform results due to variations in the mechanical properties of the tissue between different patients and variations in the way in which the tool is manipulated by a surgeon.

There is therefore a need for a surgical tool for removing a block of material from a body which would include a mechanical actuation arrangement including a number of springs for controlling deflection of the blades, thereby improving repeatability and reliability of the tissue sampling technique described in the aforementioned patent,

SUMMARY OF THE INVENTION

The present invention is a surgical tool for removing a block of material from a body.

According to the teachings of the present invention there is provided, a surgical tool for removing a block of material from a body, the surgical tool comprising a tool head including: (a) an elongated support element having a direction of elongation and configured for insertion along a first slit parallel to the direction of elongation into the material of the body; (b) a first blade assembly including: (i) a pair of arms pivotally mounted relative to the support element so as to rotate about a first axis perpendicular to the direction of elongation, a plane passing through the support element parallel to both the direction of elongation and the first axis being referred to as a tool plane, and (ii) a first blade element pivotally mounted on the arms so as to be pivotable about a second axis parallel to, but displaced from, the first axis, the first blade element including a rear cutting edge, the first blade assembly assuming an insertion state in which the pair of arms and the first blade element are deployed substantially in the tool plane, and a deflected state in which the first blade element is deployed to cut rearward in a direction forming an acute angle with the tool plane; (c) a second blade element pivotally mounted relative to the support element so as to be pivotable about a third axis substantially parallel to the first axis, the second blade element assuming an initial state in which the second blade element is deployed substantially in the tool plane and being pivotable to an inclined state in which the second blade element is arranged to cut in a direction inclined to the tool plane; and (d) a mechanical actuation arrangement including a plurality of spring elements and configured to resiliently bias the first blade assembly from the insertion state to the deflected state and to resiliently bias the second blade element from the initial state to the inclined state.

According to a further feature of the present invention, the pair of arms are integrally formed together with a bridging element.

According to a further feature of the present invention, the bridging element extends substantially along the first axis.

According to a further feature of the present invention, the pivotal mounting of the pair of arms is configured to define a fully deflected position corresponding to a final state of the first blade assembly in which the pair of arms project outwards substantially perpendicular to the tool plane.

According to a further feature of the present invention, there is also provided a locking mechanism configured for locking the pair of arms in a final position projecting outward from the support element.

According to a further feature of the present invention, the locking mechanism includes a spring element deployed for generating relative motion of at least one of the arms relative to the support element in a direction parallel to the first axis.

According to a further feature of the present invention, the spring element is implemented as a leaf spring associated with the support element.

According to a further feature of the present invention, each of the arms is formed with a cutting edge deployed such that when the pair of arms assume the outward projecting position, the cutting edges of the arms are arranged for cutting in a direction parallel to the direction of insertion.

According to a further feature of the present invention, the mechanical actuation arrangement includes a resilient projection from the support element deployed so as to bias the first blade element from the insertion state towards the deflected state.

According to a further feature of the present invention, the mechanical actuation arrangement further includes a retention element initially deployed so as to retain the first blade assembly in the insertion state and displaceable so as to release the first blade assembly to move towards the deflected state.

According to a further feature of the present invention, the mechanical actuation arrangement further includes a retention element mechanically interconnected with the elongated support element so as to be movable relative to the elongated support element between a retention position in which the at least one abutment element abuts the first blade element so as to restrain movement of the first blade assembly from the insertion state towards the deflected state and an open position in which the abutment element is removed from the blade element so as to allow movement of the first blade assembly towards the deflected state.

According to a further feature of the present invention, the first blade element has an upper surface, the mechanical actuation arrangement further including a resilient biasing arrangement deployed such that, when the pair of arms assume a final state projecting outward from the support element, the resilient biasing arrangement biases the first blade element to a position with the upper surface substantially parallel to the tool plane.

According to a further feature of the present invention, the resilient biasing arrangement includes a torsion spring deployed between at least one of the arms and the first blade element.

According to a further feature of the present invention, the mechanical actuation arrangement further includes at least one abutment surface associated with at least one of the arms and configured such that, when the first blade assembly assumes the insertion state and the deflected state, a part of the second blade element abuts the at least one abutment surface to prevent pivotal motion of the second blade element from the initial state towards the inclined state and, when the first blade assembly continues towards a final state wherein the pair of arms project outwards from the tool plane and the first blade element is spaced from the tool plane, the second blade element is released for pivotal motion towards the inclined state.

According to a further feature of the present invention, the mechanical actuation arrangement includes a spring element deployed to bias the second blade element from the initial state to the inclined state, the spring element being arranged to provide an abutment surface for part of the second blade element so as to delimit the inclined state.

According to a further feature of the present invention, the first blade element is formed with a substantially straight cutting edge.

According to a further feature of the present invention, the second blade element is formed with a substantially straight cutting edge.

According to a further feature of the present invention, there is also provided a handle for manipulating the elongated support element, wherein the support element is formed with a shank portion including a locking tab resiliently biased to a projecting position, and wherein the handle is formed with a channel for receiving the shank portion, the channel including a lateral recess for receiving the locking tab, such that, when the shank portion is inserted into the channel, the locking tab is temporarily deformed and, on reaching the lateral recess, deploys resiliently into engagement with the lateral recess, thereby retaining the support element in engagement with the handle.

According to a further feature of the present invention, the locking tab and the lateral recess are deployed such that the support element is not readily removable from the handle in a non-destructive manner.

According to a further feature of the present invention, the mechanical actuation arrangement further includes a retention pin mechanically interconnected with the elongated support element so as to be movable relative to the elongated support element between a retention position in which the at least one retention pin abuts the first blade element so as to restrain movement of the first blade assembly from the insertion state towards the deflected state and an open position in which the retention pin is removed from the blade element so as to allow movement of the first blade assembly towards the deflected state, wherein displacement of the retention pin from the retention position to the open position when the support element is engaged with the handle requires flexing of the retention pin.

BRIEF DESCRIPTION OF THE DRAWINGS

The invention is herein described, by way of example only, with reference to the accompanying drawings, wherein:

FIGS. 3A-3F are isometric views of the tool head from the surgical tool of FIG. 1 with the handle omitted showing a sequence of states of the tool employed during removal of a block of tissue according to the teachings of the present invention;

FIG. 3G is an enlarged view of a region of FIG. 3F identified by rectangle "G";

DESCRIPTION OF THE PREFERRED EMBODIMENTS

Figure 1:
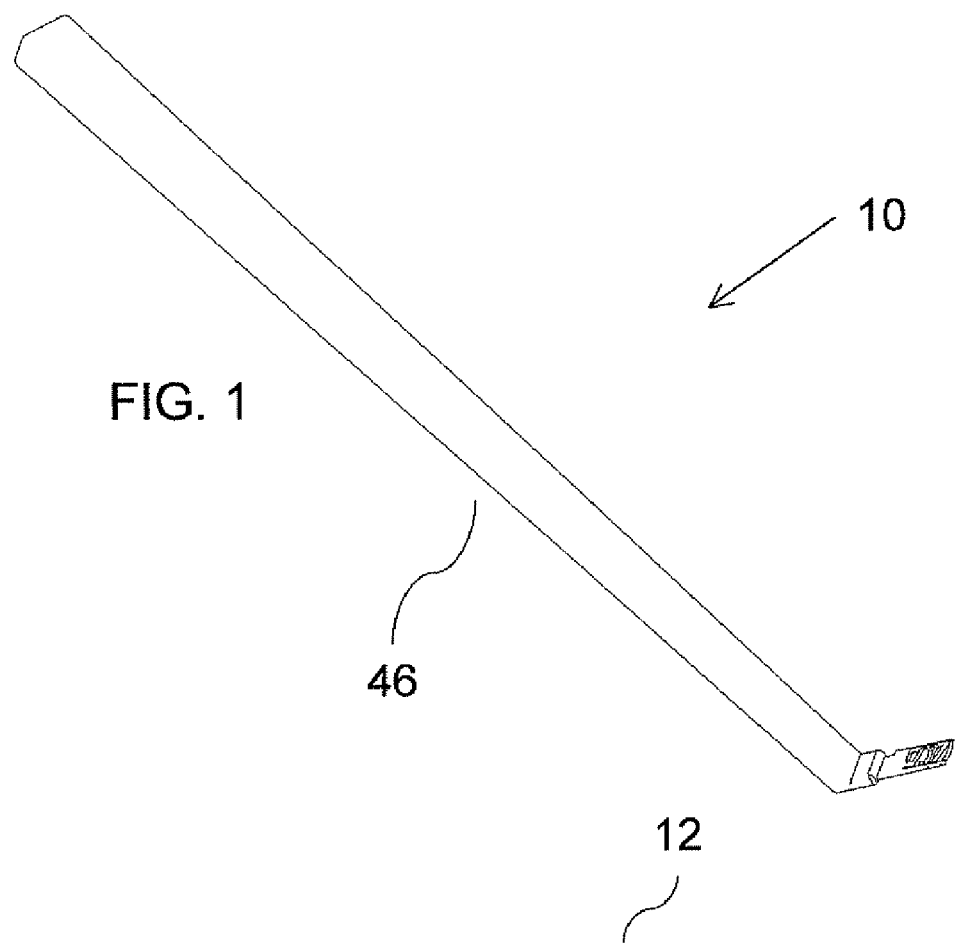
FIG. 1 is an isometric view of surgical tool, constructed and operative according to the teachings of the present invention, for removing a block of material from a body, the surgical tool having a handle and a tool head.

The present invention is a surgical tool for removing a block of tissue or other material from an organ or other body.

The principles and operation of surgical tools according to the present invention may be better understood with reference to the drawings and the accompanying description.

Referring now to the drawings, FIGS. 1-6D illustrate the structure and function of a surgical tool, generally designated 10, constructed and operative according to the teachings of the present invention, while FIGS. 7A-7F illustrate the use of tool 10 for removal of a block of material from a body, in a particularly preferred but non-limiting example of the human eye.

Generally speaking, tool 10 has a tool head 12 including an elongated support element 14 configured for insertion along a first slit parallel to a direction of elongation of support element 14 into the tissue of the organ. A first blade assembly 16 includes a pair of arms 18a, 18b which are pivotally mounted relative to support element 14 so as to rotate about a first axis 20 perpendicular to the direction of elongation of support element 14. For convenience of description, a plane passing through support element 14 parallel to both the direction of elongation and first axis 20 is referred to as a "tool plane". Pivotally mounted on arms 18a, 18b is a first blade element 22 which pivots about a second axis 24 parallel to, but displaced from, first axis 20. First blade element 22 has a rear cutting edge. Tool head 12 also includes a second blade element 26 pivotally mounted relative to support element 14 so as to be pivotable about a third axis 28 substantially parallel to first axis 20.

It is a particularly feature of surgical tool 10, in contrast to the tool described in the aforementioned U.S. Pat. No. 7,041, 114, that movements of the various blade elements of tool 10 are performed under biasing of a mechanical actuation arrangement including a plurality of spring elements This provides a degree of reliability and repeatability in performance of the surgical procedure which cannot be achieved with the prior device.

Figure 3A:
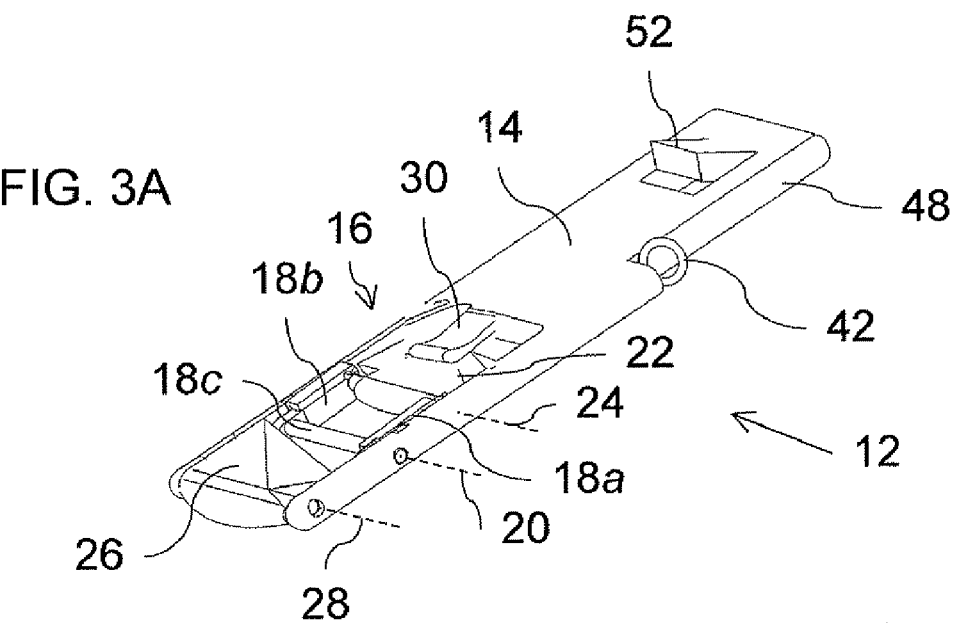
Figure 3B:
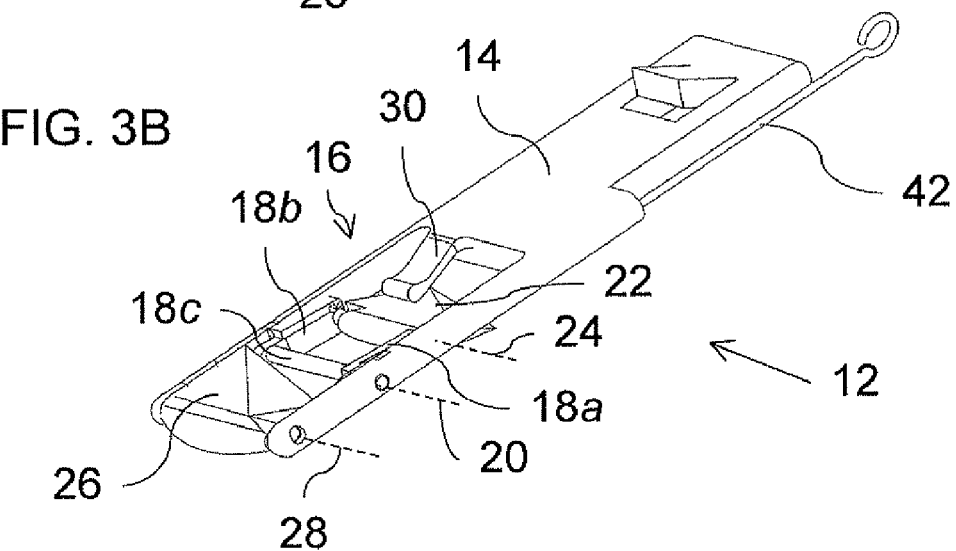
Figure 3C:
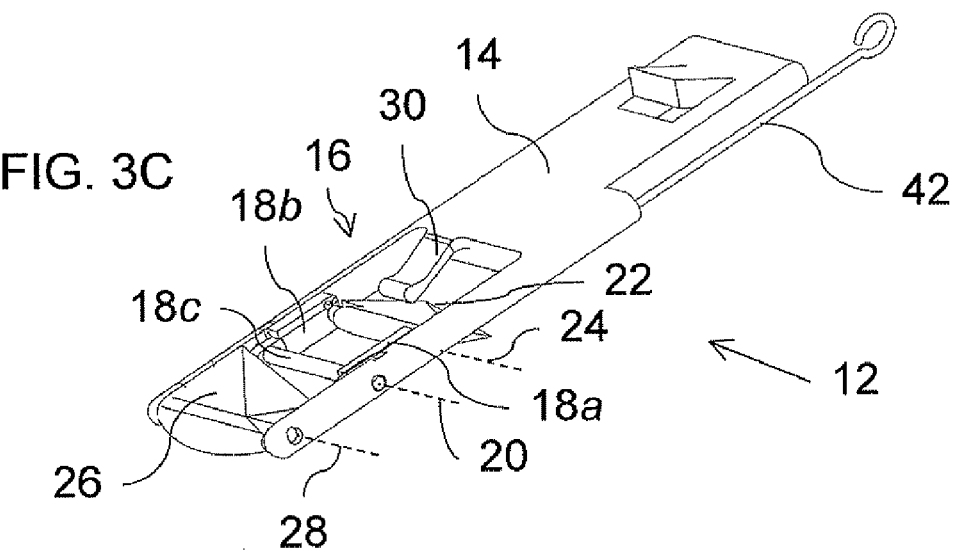

Specifically, the mechanical actuation arrangement is configured to resiliently bias first blade assembly 16 from an insertion state (FIGS. 3A and 6A) in which pair of arms 18a, 18b and first blade element 22 are deployed substantially in the tool plane towards a deflected state (FIGS. 3B-3D and 6B) in which first blade element 22 is deployed to cut rearward in a direction forming an acute angle with the tool plane. This deflection is preferably achieved by a resilient projection 30 from support element 14, as seen in FIGS. 3A and 3B.

Figure 4A:
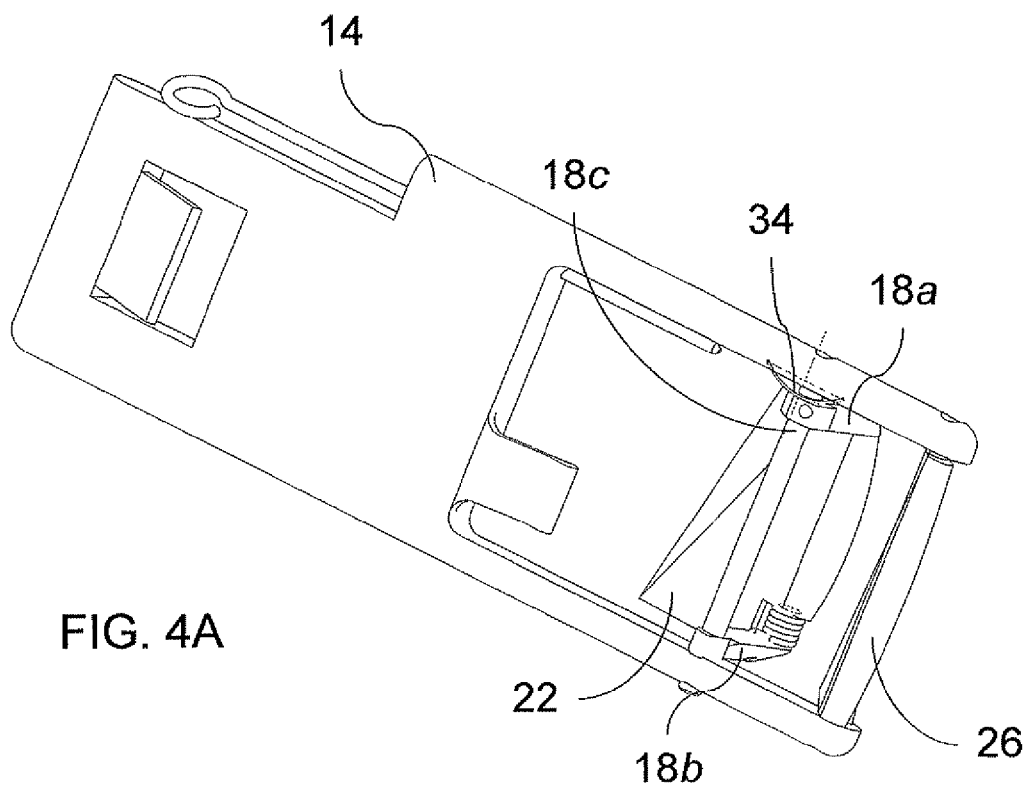
FIGS. 4A and 4B are upper and lower isometric views, respectively, of the tool head in the final state of FIG. 3F.
Figure 4B:
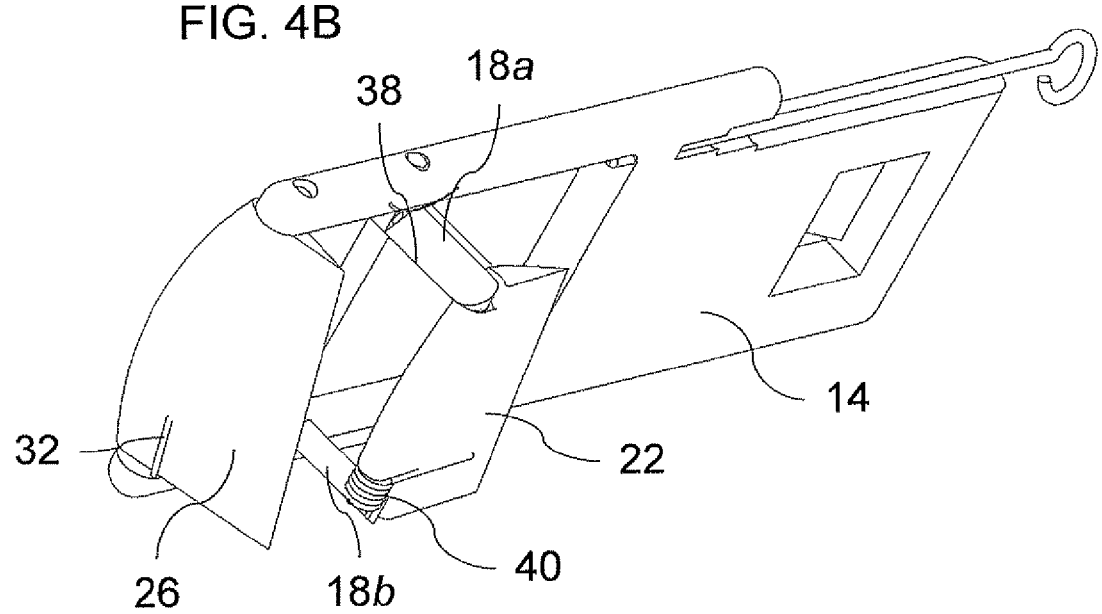

The mechanical actuation arrangement is also configured to resiliently bias second blade element 26 from an initial state (FIGS. 3E and 6C) in which second blade element 26 is deployed substantially in the tool plane towards an inclined state (FIGS. 3F and 6D) in which second blade element 26 is arranged to cut in a direction inclined to the tool plane. This deflection is preferably achieved by a spring rod 32 projecting from support element 14, as seen in FIGS. 3F and 4B.

At this stage, it will be appreciated that the present invention provides a surgical tool for extraction of a block of tissue which maintains all of the advantageous features of the techniques of the aforementioned patent as set out therein while at the same time offering significant advantages with regard to reliability and repeatability of the various blade motions. This and other advantages of the present invention will become clearer from the following detailed description.

It will now be helpful to define certain terminology as used herein in the description and claims. Firstly, reference is made to a "block" of tissue cut by the present invention. The term "block" is used herein to refer to any block or chunk of any shape. The block of tissue cut by the present invention is typically defined by an upper surface cut during or prior to insertion of the tool, a pair of side surface roughly perpendicular to the upper surface, front and rear surfaces which may be arcuate and which are acutely inclined relative to the upper surface and, in the case of a hollow organ, a naturally occurring lower surface.

The block of material cut by the present invention may be sampled from any organ or other part of the body. In the preferred example of the ocular surgery technique illustrated here, the organ is a hollow organ, which may be liquid filled or gas filled. In this case, the block removed by the tool of the present invention is preferably a block adjacent to the interior surface of the organ wall, i.e., the surface on the far side from which the tool is inserted, to form a block bounded in part by the naturally occurring interior surface. In the case of a non-hollow organ, or where sampling from an intermediate depth from the wall of a hollow organ, first blade element 22 is modified by addition of a front cutting edge to cut the lower surface of the block, as will be clear to one ordinarily skilled in the art. Other applications include, but are not limited to, removal of lesions from healthy tissue, and removal of plaque from within blood vessels.

Figure 2:
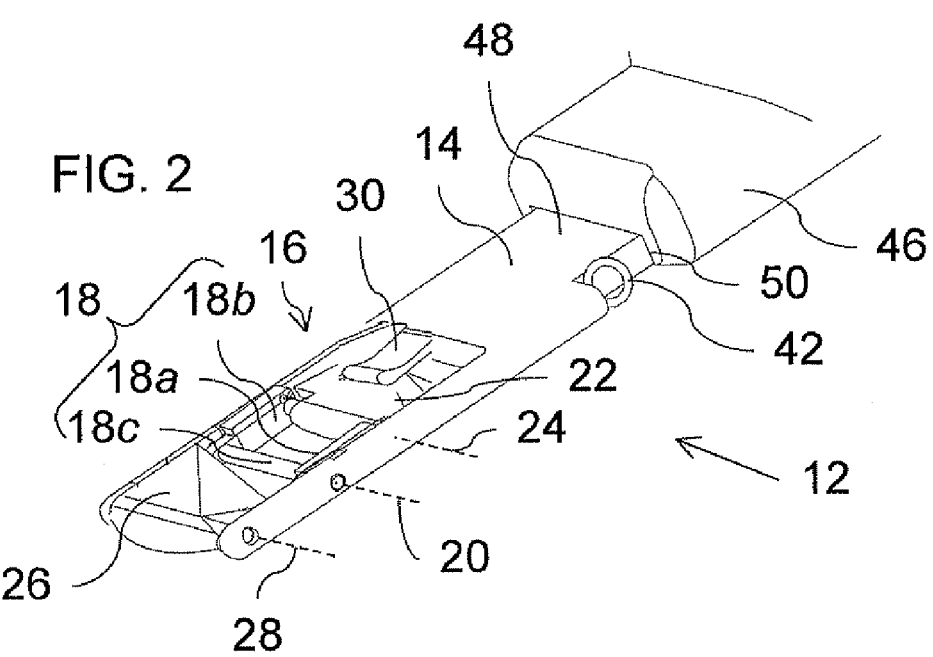
FIG. 2 is an enlarged isometric view of the part of the surgical tool of FIG. 1 including the tool head.
Figure 6A:
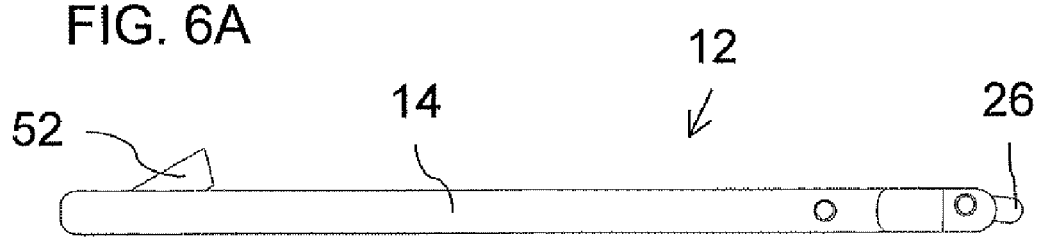
FIGS. 6A-6D are side views of the tool head of FIG. 1 in states corresponding to FIG. 3A, FIG. 3D, an additional intermediate state and FIG. 3F, respectively.
Figure 6B:
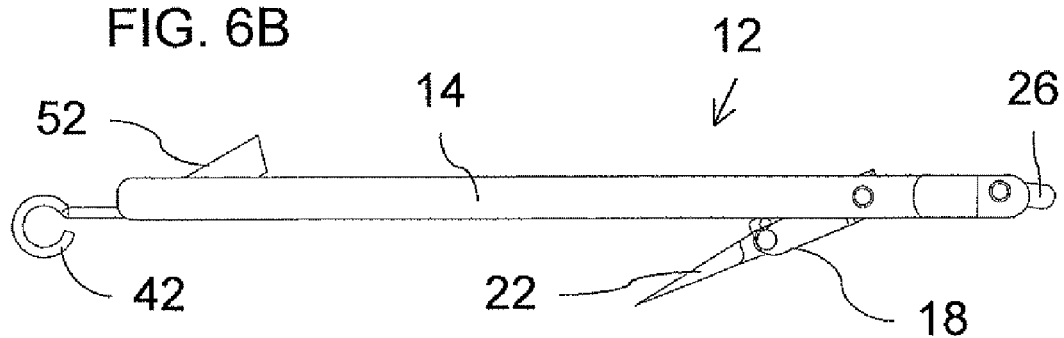
Figure 6C:
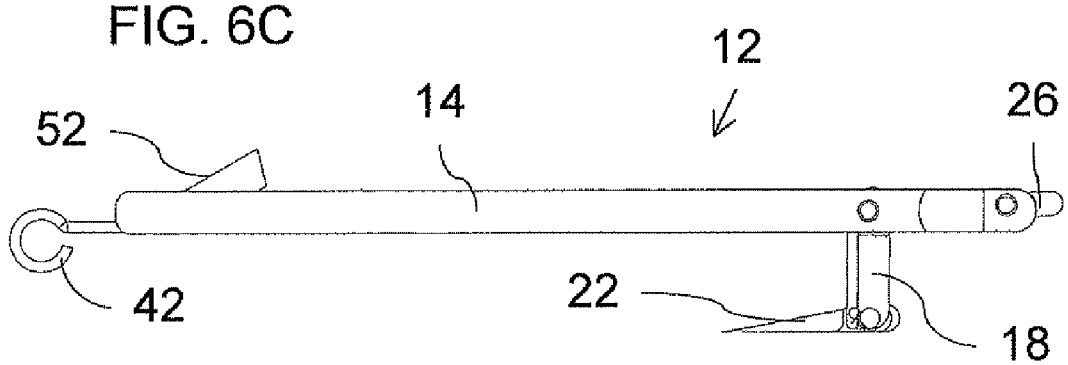
Figure 6D:
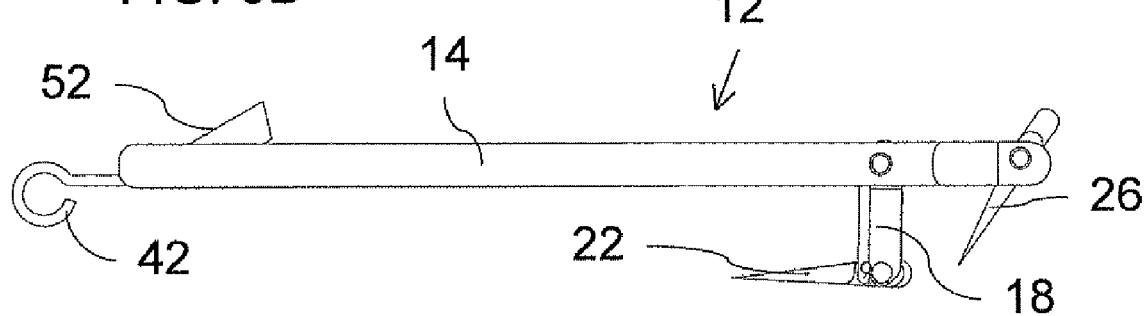

In describing surgical tool 10, reference is made to various directions. The "front" of the device is taken to be the portion of the device which is inserted first into the tissue, corresponding to the region of second blade element 26, whereas "rear" or "back" are used to refer to the part of tool head 12 which attaches to the handle (to be described below). Similarly, "forward" or "frontward" refer to directions in which the front of the device leads, such as motion in the direction of insertion into the tissue, while "rearward" or "backward" refer to motions occurring during partial or full withdrawal of the device. "Down", "downward", "lower" or the like are used to refer to the direction in which the blade assembly opens and "up", "upward", "higher" or the like for the opposite direction, although it will be clear that these labels are given for convenience of reference only, and that the device may actually be used in any orientation.

Where axes or planes are referred to as "substantially parallel" or "substantially perpendicular", the terminology should be interpreted to encompass whatever degree of deviation from parallelism or perpendicularity which maintains the functionality of the structure described. Thus, with regard to the axes or rotation of the arms and blades, a deviation of 10 or even 20 degrees from parallelism of the axes may not significantly impact the function of the device, and is for present purposes defined as "substantially parallel." Similarly, the final position of the first blade element described below as substantially parallel to the tool plane may vary from precise parallelism by as much as 20 or even 30 degrees while still providing the desired function of an underlying support surface for the cut block of tissue, and is therefore described as "substantially parallel."

Where reference is made to an element or elements lying in a certain plane or being "in-plane," the terminology should be understood in the normal intuitive sense that the elements in question are arranged more-or-less in the plane in question, or do not project significantly from the plane. Clearly, in purely mathematical terms, a three-dimensional object cannot truly lie within a plane, which only has two dimensions. In the specific case of elements described as lying within the "tool plane," this indicates that the elements lie substantially within the thickness of the elongated support element, thereby giving the tool head a generally flat appearance as seen in FIGS. 2, 3A and 6A.

Where reference is made to "springs" or "spring elements," it should be understood that these refer to any arrangement which provides resilient bias of the required type. The springs may be integral portions of larger structural elements which employ inherent elastic properties of the material to provide spring functionality, or may be separate spring elements attached or inserted in the appropriate positions. The springs may be of any suitable material including, but not limited to, metals, metal alloys and polymers.

Where reference is made to a "pin" or "retention pin" employed to lock certain elements against motion prior to removal, it should be noted that the pin is defined functionally by its suitability to insert and withdraw from the locking channel and need not have any particular geometrical form. Thus, the pin may be implemented as a round pin, a square cross-section pin, a flat strip or any other geometrical form effective for fulfilling the stated function.

Turning now to the features of surgical tool 10 in more detail, pair of arms 18a, 18b are preferably integrally formed together with a bridging element 18c as a single piece. This ensures that pivotal motion of the two arms occurs together in step. Typically, bridging element 18c extends substantially along first axis 20, serving as an axle. At the end of the surgical procedure, bridging element 18c also helps to retain the cut block of tissue from escaping from the upper side of the device. The combination of arms 18a, 18bb and bridging element 18c is referred to for conciseness as arm rotor 18.

Figure 5A:
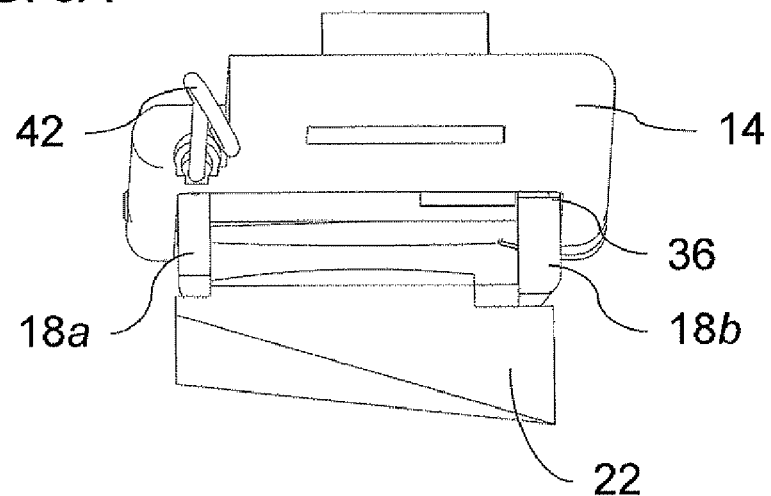
FIG. 5A and 5B are lower rear views of the tool head of FIG. 1 showing a preferred form of a locking mechanism for an arm rotor of the tool head.
Figure 5B:
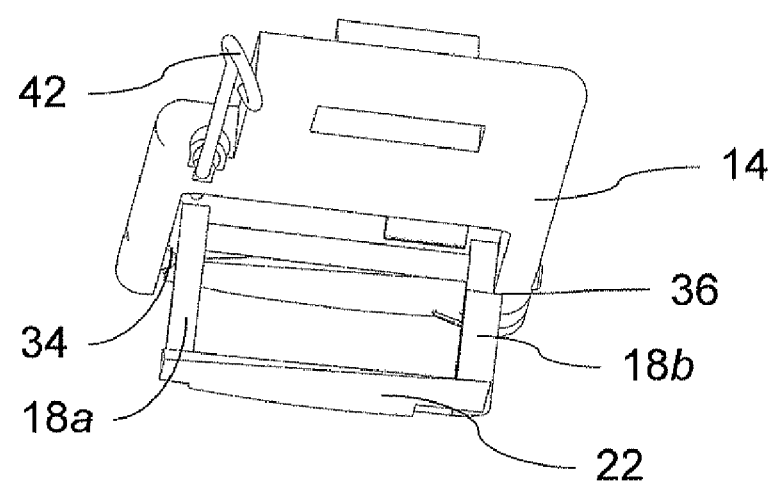

Arm rotor 18 is pivotally mounted to support element 14 which is preferably implemented with two parallel bars into which axial pins of arm rotor 18 extend, Arm rotor 18 preferably has a well defined fully deflected position in which arms 18a, 18b project outwards substantially perpendicular to the tool plane. Most preferably, a locking mechanism is configured for locking arm rotor 18 in the fully deflected position. One particularly preferred implementation of this locking mechanism is best seen in FIGS. 5A and 5B According to this implementation, the locking mechanism includes a spring element deployed for generating relative motion of at least one of arms 18a, 18b, and typically the entirety of arm rotor 18, relative to support element 14 in a direction parallel to first axis 20. In the case illustrated, the spring element is implemented as a leaf spring 34 interposed between arm rotor 18 and support element 14 so as to bias arm rotor 18 to move axially. Arm 18b is formed with a laterally projecting shoulder 36 initially abutting the inside of the bar of support element 14 so as to prevent lateral movement of arm rotor 18, as shown in FIG. 5A. Shoulder 36 is configured so that, when arm 18b reaches its fully deflected position, shoulder 36 clears the lower edge of the bar of support element 14, allowing spring 34 to displace arm rotor 18 a small distance along axis 20. As a result of this motion, shoulder 36 becomes lodged under the bar of support element 14, thereby locking arm rotor 18 in its fully deflected 10 position, as shown in FIG. 5B.

Arms 18a, 18b preferably also perform the function of side blades for cutting the side edges of the block of tissue. For this purpose, each arm is preferably formed with a cutting edge 38 deployed such that, when arms 18a, 18b assume their outward projecting fully deflected positions, cutting edges 38 are arranged for cutting in a forward direction parallel to the direction of insertion.

Motion of first blade element 22 is controlled primarily by two spring elements. Resilient projection 30 provides the initial deflection for first blade element 22 to start cutting into the tissue. The mechanical actuation arrangement also includes a resilient biasing arrangement deployed between one or both of arms 18a, 18b and first blade element 22 biasing the blade element to a position roughly perpendicular to the arms. Most preferably, this resilient biasing arrangement is implemented as a torsion spring, such as the helical torsion spring 40 visible in FIGS. 4A and 4B. As a result, when arm rotor 18 assumes its fully deflected final position, first blade element 22 tends towards a position with its upper surface substantially parallel to the tool plane (FIGS. 3F, 6C and 6D), providing a lower surface for supporting the cut block of tissue.

Figure 5C:
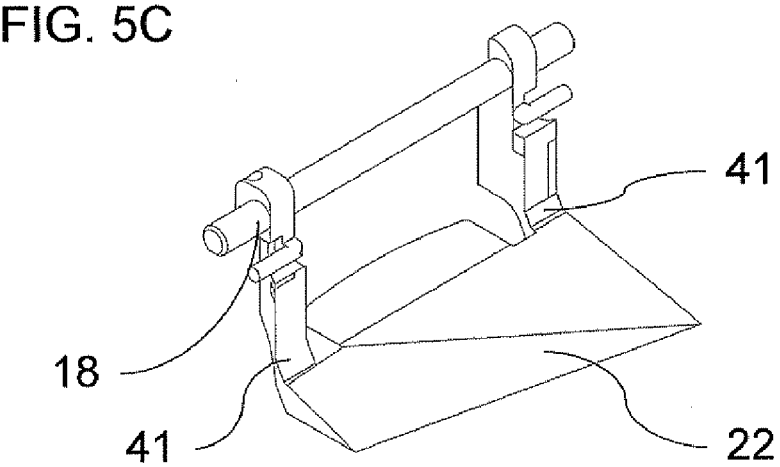
FIG. 5C is an isometric view of an alternative implementation of a first blade assembly for use in the tool head of FIG. 1.

Parenthetically, referring to FIG. 5C, it should be noted that one or more of the pivotal connections of tool head 12 may optionally be implemented using an integral hinge, thereby reducing the number of components to be assembled during manufacture. By way of one non-limiting example, FIG. 5C illustrates an alternative implementation of arm rotor 18 and first blade element 22 in which they are integrally formed as a single element hinged at integral hinge 41.

In order to keep the tool head in its flat insertion state and prevent premature deployment of the blades of tool head 12, the mechanical actuation arrangement preferably includes a retention element or pin 42 initially deployed so as to retain the first blade assembly in the insertion state and displaceable so as to release the first blade assembly to move towards the deflected state. Although tool head 12 is preferably designed so as to ensure sequential deployment of the first and second blade elements, as an additional safety precaution, pin 42 is preferably implemented extending along support element 14 so as to abut both first and second blade elements 22 and 26, thereby preventing their premature deployment.

The preferred sequence of operations to be performed by surgical tool 10 (to be detailed below) requires second blade 26 to be deflected only at the end of the first incision performed by first blade assembly 16. To this end, the mechanical actuation arrangement preferably also includes at least one abutment surface 44 (see FIG. 3G) associated with at least one of arms 18a, 18b and configured such that, when first blade assembly 16 assumes its insertion state and its deflected state, a part of second blade element 26 abuts abutment surface 44 to prevent pivotal motion of second blade element 26 towards its inclined state and, when first blade assembly 16 assumes its final state, second blade element 26 is released for pivotal motion towards its inclined state.

From the above description, it will be noted that the deflection of both blade elements 22 and 26 so as to cut into the tissue is achieved by the mechanical actuation arrangement without requiring the specially shaped blade features of the aforementioned prior patent. Instead, both blades are preferably formed with substantially straight cutting edges, typically with one or two segments, which lie in a plane with the body of the blade. This renders the blades much easier to manufacture, and allows optimization of the cutting geometry.

Turning now to actuation of second blade element 26, as mentioned above, deflection of second blade element 26 is preferably achieved by a spring rod 32 projecting one side bar of support element 14, as best seen in FIGS. 3F and 4B. In the implementation shown here, spring rod 32 is deployed in front of axis 28 and applies an upward force on the underside of a front part of second blade element 26, thereby forcing the rear cutting edge downwards. Most preferably, spring rod 32 is also configured to delimit a fully deflected position of second blade element 26. This may be achieved as shown by deploying spring rod 32 projecting from a location below axis 28 such that, as second blade element 26 reaches a predefined desired angle, the lower surface of the blade element comes into abutment with base of spring rod 32, thereby blocking further rotation. Clearly, spring element 32 may alternatively be implemented in various other forms, for example, employing a leaf spring or a torsion spring, and corresponding alternative arrangements for defining the fully deflected end position may readily be implemented by one ordinarily skilled in the art.

For procedures such as the ocular surgery technique described herein, tool head 12 is preferably manipulated by attachment to a handle 46. For design reasons, handle 46 is typically produced from low cost materials such as various plastics, Accordingly support element 14 is preferably formed with a shank portion 48 which engages within a corresponding channel 50 of handle 46. In the preferred implementation shown here, shank portion 48 includes a locking tab 52 resiliently biased to a projecting position (see FIG. 3A) and channel 50 is formed With a corresponding lateral recess (not seen). The lateral recess is configured such that, when shank portion 48 is inserted into channel 50, locking tab 52 is temporarily deformed and, on reaching the lateral recess, deploys resiliently into engagement with the lateral recess, thereby retaining support element 14 in engagement with handle 46.

For reasons of sterility, it is preferable that both tool head 12 and handle 46 are disposable items limited to a single use. To this end, locking tab 52 and the corresponding lateral recess are preferably deployed such that support element 14 is not readily removable from handle 46 in a non-destructive manner. As an additional precaution against repeated use, a particularly preferred implementation of retention pin 42 is configured such that displacement from its retention position to its open position when support element 14 is engaged with handle 46 requires flexing of retention pin 42. Thus, when pin 42 is inserted during manufacture of tool head 12 prior to attachment to handle 46, it is inserted along a straight path. However, after attachment to handle 46, and attempt at reinsertion of pin 42 would be hampered by the difficulty of inserting a very fine flexible pin along an arcuate path.

It will be noted that surgical tool 10 may be implemented with different dimensions according to the intended application and the size of block which is to be removed, typically ranging from a width of about 1 millimeter up to several centimeters. However, it is significant to point out that the tool is especially advantageous for applications where the dimensions of block to be cut are smaller than could readily be achieved in a reproducible manner by manual procedures performed without the tool of the present invention. For example, in the particularly preferred ocular surgery application described herein, the width of tool head 12 is preferably no more than about 3 millimeters, and the length and height of the block cut are typically no more than about 2 millimeters and 1 millimeter, respectively. For certain other applications, such as certain intravascular applications, a width of about 1.5 millimeters may be preferred.

The surgical tool of the present invention may be implemented using any suitable materials known in the field of medical devices. Typical examples for the components of tool head 12 are surgical stainless steel and nitinol alloys, either or which are capable of providing a medical device with sharp cutting edges and with sufficient inherent elasticity to provide integral spring elements as disclosed. Typical materials for handle 46 are various medical grade polymer materials.

Figure 7A:
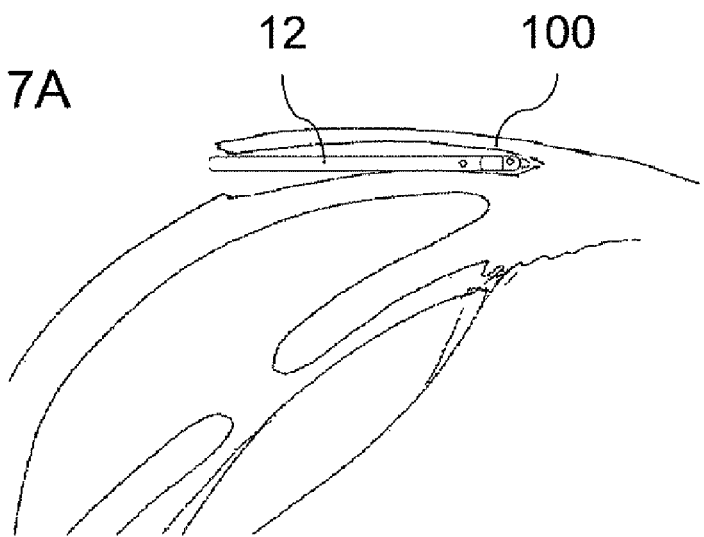
FIGS. 7A-7F are schematic representations of stages in the removal of a block of tissue from the human eye employing the tool of FIG. 1 according to the teachings of the present invention.

Turning now to FIGS. 7A-7F, these show the sequence of movements for performance of a particularly preferred ocular surgery procedure using surgical tool 10. For clarity of presentation, handle 46 has been omitted. FIG. 7A shows the initial insertion of tool head 12 into a slit 100 formed in the corneal tissue. The slit is preferably formed by a separate tool prior to insertion of tool head 12, although an implementation with a front blade edge on second blade element 26 for cutting the initial slit also falls within the scope of the present invention.

Figure 7B:
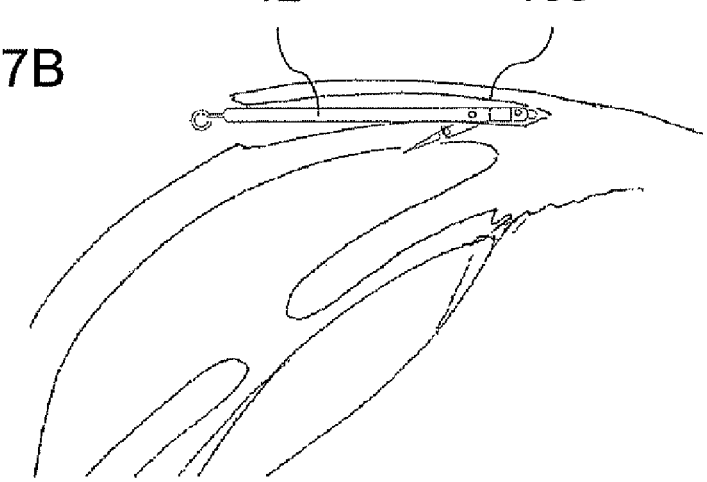
Figure 7C:
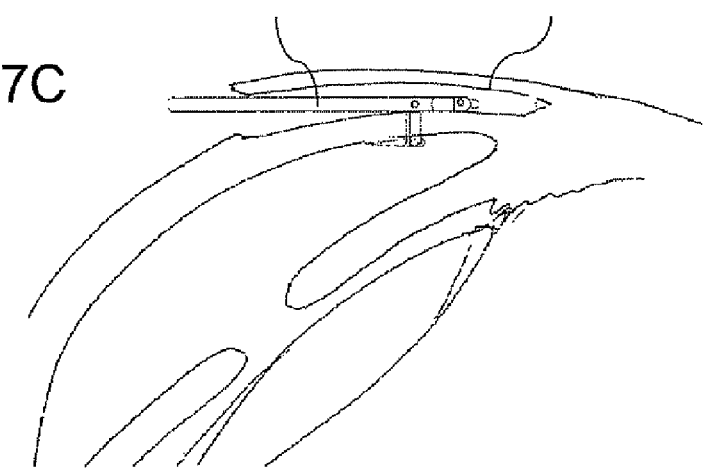

Retention pin 42 is then withdrawn, releasing first blade assembly 16 to be depressed by resilient projection 30 so as to deflect the cutting edge of first blade element 22 downwards towards the underlying tissue. Tool head 12 is then withdrawn along the initial slit, causing first blade element 22 to cut a rearward downward slit as shown in FIG. 7B, forming the rear surface of the block of tissue. During this motion, the presence of tissue on either side of first blade element 22 keeps the blade aligned to cut a straight slit as shown.

Then, as first blade element 22 clears the tissue into the cavity of the eye, torsion spring 40 causes first blade element 22 to rotate (clockwise as shown) while pressure of compressed tissue on the blunt rear edges of arms 18a and 18b displaces them to their fully opened positions where they are locked by the locking mechanism described above. The result is the position of FIG. 7C, corresponding to the state of tool head 12 shown in FIG. 6C. As the arms reach their fully opened positions, abutment surface 44 releases second blade element 26 to deflect under action of spring rod 32, but the presence of tissue underlying the blade prevents significant deflection of the blade.

Tool head 12 is then advanced along the slit. During this motion, the cutting edges of arms 18a and 18b cut the side surfaces of the tissue block. First blade element 22 moves forward through the fluid-filled eye cavity until reaching the angle of the eye, defining the fully advanced position of the tool. During this motion, second blade element 26 slides across the underlying tissue with its cutting edge trailing.

Figure 7D:
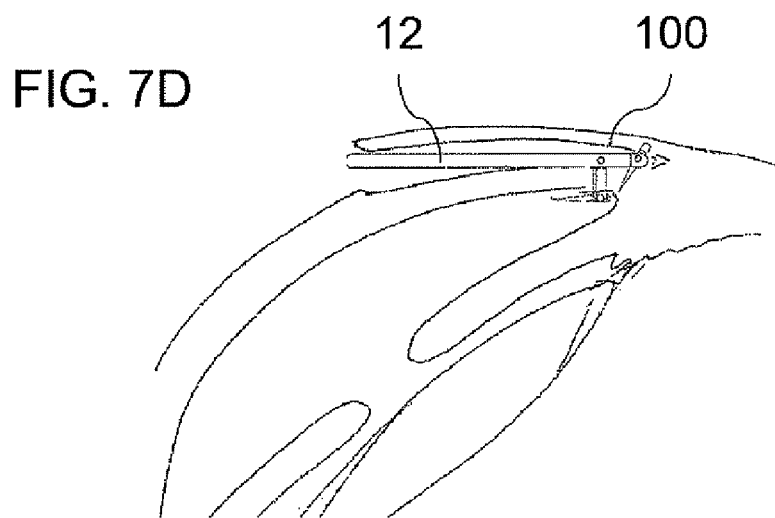
Figure 7E:
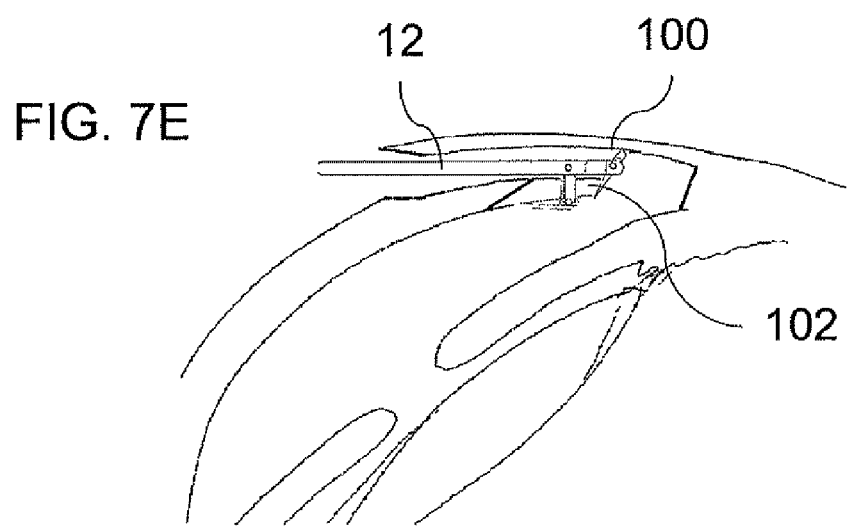

Tool head 12 is then moved in a second withdrawing motion. During this motion, second blade element 26 cuts downwards into the tissue under the action of spring rod 32, thereby cutting the front surface of the block of tissue as shown in FIG. 7D. The tissue block 102 is thus severed and remains held within the tool head, supported from below by the upper surface of first blade element 22, from the sides by arms 18a and 18b, from above by bridging element 18c and at its end by second blade element 26. The trapped block of tissue 102 is then removed together with tool head 12 (FIG. 7E), typically facilitated by insertion of a spatula (not shown) beneath the cutting blades.

Figure 7F:
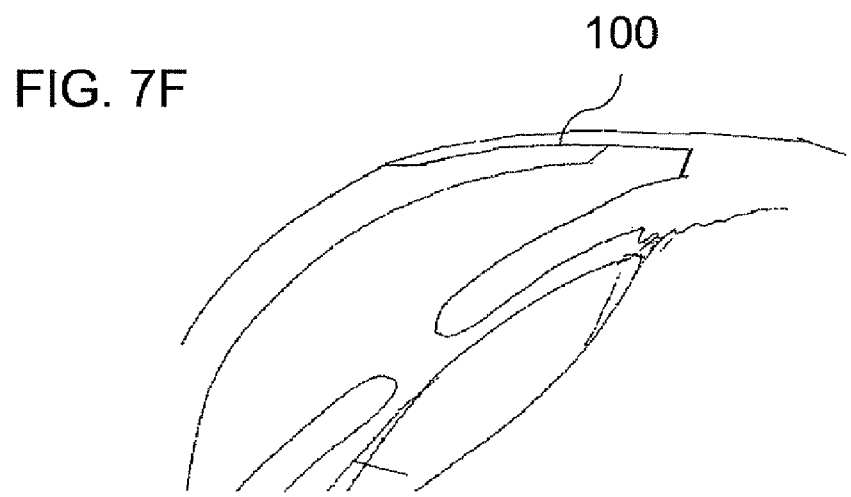

After removal of the tool, the remaining tissue of the eye returns to its unstretched form as shown in FIG. 7F, thereby sealing the incisions.

Although described herein with reference to an exemplary ocular surgery technique, as mentioned earlier, the surgical tool of the present invention may be used for a wide range of other procedures. By way of one non-limiting example, tool head 12 may be mounted at the tip of a catheter and used within blood vessels to remove plaque from the inner surface of the vessel. Similarly, catheter-mounted implementations of the invention may be employed to perform biopsies from the stomach, the large intestine or the bladder.

It will be appreciated that the above descriptions are intended only to serve as examples, and that many other embodiments are possible within the scope of the present invention as defined in the appended claims.

What is claimed is:

1. A surgical tool for removing a block of material from a body, the surgical tool comprising a tool head including:
   (a) an elongated support element having a direction of elongation and configured for insertion along a first slit parallel to said direction of elongation into the material of the body;
   (b) a first blade assembly including:
      (i) a pair of arms pivotally mounted relative to said support element so as to rotate about a first axis perpendicular to said direction of elongation, a plane passing through said support element parallel to both said direction of elongation and said first axis being referred to as a tool plane, and
      (ii) a first blade element pivotally mounted on said arms so as to be pivotable about a second axis parallel to, but displaced from, said first axis, said first blade element including a rear cutting edge,
   said first blade assembly assuming an insertion state in which said pair of arms and said first blade element are deployed substantially in said tool plane, and a deflected state in which said first blade element is deployed to cut rearward in a direction forming an acute angle with said tool plane;
   (c) a second blade element pivotally mounted relative to said support element so as to be pivotable about a third axis substantially parallel to said first axis, said second blade element assuming an initial state in which said second blade element is deployed substantially in said tool plane and being pivotable to an inclined state in which said second blade element is arranged to cut in a direction inclined to said tool plane; and
   (d) a mechanical actuation arrangement including a plurality of spring elements and configured to resiliently bias said first blade assembly from said insertion state to said deflected state and to resiliently bias said second blade element from said initial state to said inclined state.

2. The surgical tool of claim 1, wherein said pair of arms are integrally formed together with a bridging element.

3. The surgical tool of claim 2, wherein said bridging element extends substantially along said first axis.

4. The surgical tool of claim 1, wherein said pivotal mounting of said pair of arms is configured to define a fully deflected position corresponding to a final state of said first blade assembly in which said pair of arms project outwards substantially perpendicular to said tool plane.

5. The surgical tool of claim 1, further comprising a locking mechanism configured for locking said pair of arms in a final position projecting outward from said support element.

6. The surgical tool of claim 5, wherein said locking mechanism includes a spring element deployed for generating relative motion of at least one of said arms relative to said support element in a direction parallel to said first axis.

7. The surgical tool of claim 6, wherein said spring element is implemented as a leaf spring associated with said support element.

8. The surgical tool of claim 5, wherein each of said arms is formed with a cutting edge deployed such that, when said pair of arms assume said outward projecting position, said cutting edges of said arms are arranged for cutting in a direction parallel to said direction of insertion.

9. The surgical tool of claim 1, wherein said mechanical actuation arrangement includes a resilient projection from said support element deployed so as to bias said first blade element from said insertion state towards said deflected state.

10. The surgical tool of claim 9, wherein said mechanical actuation arrangement further includes a retention element initially deployed so as to retain said first blade assembly in said insertion state and displaceable so as to release said first blade assembly to move towards said deflected state.

11. The surgical tool of claim 1, wherein said mechanical actuation arrangement further includes a retention element mechanically interconnected with said elongated support element so as to be movable relative to said elongated support element between a retention position in which said at least one abutment element abuts said first blade element so as to restrain movement of said first blade assembly from said insertion state towards said deflected state and an open position in which said abutment element is removed from said blade element so as to allow movement of said first blade assembly towards said deflected state.

12. The surgical tool of claim 1, wherein said first blade element has an upper surface, said mechanical actuation arrangement further including a resilient biasing arrangement deployed such that, when said pair of arms assume a final state projecting outward from said support element, said resilient biasing arrangement biases said first blade element to a position with said upper surface substantially parallel to said tool plane.

13. The surgical tool of claim 12, wherein said resilient biasing arrangement includes a torsion spring deployed between at least one of said arms and said first blade element.

14. The surgical tool of claim 1, wherein said mechanical actuation arrangement further includes at least one abutment surface associated with at least one of said arms and configured such that, when said first blade assembly assumes said insertion state and said deflected state, a part of said second blade element abuts said at least one abutment surface to prevent pivotal motion of said second blade element from said initial state towards said inclined state and, when said first blade assembly continues towards a final state wherein said pair of arms project outwards from said tool plane and said first blade element is spaced from said tool plane, said second blade element is released for pivotal motion towards said inclined state.

15. The surgical tool of claim 1, wherein said mechanical actuation arrangement includes a spring element deployed to bias said second blade element from said initial state to said inclined state, said spring element being arranged to provide an abutment surface for part of said second blade element so as to delimit said inclined state.

16. The surgical tool of claim 1, wherein said first blade element is formed with a substantially straight cutting edge.

17. The surgical tool of claim 1, wherein said second blade element is formed with a substantially straight cutting edge.

18. The surgical tool of claim 1, further comprising a handle for manipulating said elongated support element, wherein said support element is formed with a shank portion including a locking tab resiliently biased to a projecting position, and wherein said handle is formed with a channel for receiving said shank portion, said channel including a lateral recess for receiving said locking tab, such that, when said shank portion is inserted into said channel, said locking tab is temporarily deformed and, on reaching said lateral recess, deploys resiliently into engagement with said lateral recess, thereby retaining said support element in engagement with said handle.

19. The surgical tool of claim 18, wherein said locking tab and said lateral recess are deployed such that said support element is not readily removable from said handle in a non-destructive manner.

20. The surgical tool of claim 19, wherein said mechanical actuation arrangement further includes a retention pin mechanically interconnected with said elongated support element so as to be movable relative to said elongated support element between a retention position in which said at least one retention pin abuts said first blade element so as to restrain movement of said first blade assembly from said insertion state towards said deflected state and an open position in which said retention pin is removed from said blade element so as to allow movement of said first blade assembly towards said deflected state, wherein displacement of said retention pin from said retention position to said open position when said support element is engaged with said handle requires flexing of said retention pin.

\* \* \* \* \*